United States Patent [19]

Okado et al.

[11] Patent Number: 4,544,793

[45] Date of Patent: Oct. 1, 1985

[54] CRYSTALLINE ZEOLITE, METHOD OF PREPARING SAME AND PROCESS FOR THE PRODUCTION OF OLEFINS USING SAME AS CATALYST

[75] Inventors: Hideo Okado, Ushiku; Kazuo Hashimoto, Ube; Kichinari Kawamura, Tsuchiura; Yasuyoshi Yamazaki, Yatabe; Haruo Takaya, Abiko, all of Japan

[73] Assignee: Director-General of Agency of Industrial Science and Technology, Tokyo, Japan

[21] Appl. No.: 553,257

[22] Filed: Nov. 18, 1983

[30] Foreign Application Priority Data

Nov. 24, 1982 [JP] Japan .................... 57-205839

[51] Int. Cl.⁴ .................................. C07C 1/00
[52] U.S. Cl. .......................... 585/640; 585/733
[58] Field of Search ............................ 585/640

[56] References Cited

U.S. PATENT DOCUMENTS 3,702,886 11/1972 Argauer et al. ............ 423/328
3,941,871 3/1976 Dwyer et al. .
4,049,573 9/1977 Kaeding .................... 585/640

Primary Examiner—Curtis R. Davis
Attorney, Agent, or Firm—Pahl, Lorusso & Loud

[57] ABSTRACT

A crystalline aluminosilicate having the following empirical formula:

$$xM_2O \cdot yM'O \cdot Al_2O_3 \cdot zSiO_2 \cdot nH_2O$$

wherein M is an exchangeable cation selected from the group consisting of alkali metals, hydrogen and mixtures thereof, M' is an alkaline earth metal, x is between 0 and 1.5, y is between 0.2 and 40, z is between 12 and 3000 and n is between 0 and 40 and wherein $x+y$ is 1.2 or more, said aluminosilicate having the X-ray diffraction lines of Table 1 of the specification. The crystalline aluminosilicate material is obtained by providing a reaction mixture containing water, a tetrapropylammonium compound and a source of an alkali metal oxide, an oxide of silicon, an oxide of aluminum and an oxide of an alkaline earth metal and having a composition falling within the following ranges:

$SiO_2/Al_2O_3$ molar ratio: 12–3000
$OH^-/SiO_2$ molar ratio: 0.02–10
$H_2O/SiO_2$ molar ratio: 1–1000
tetrapropylammonium ion/$SiO_2$ molar ratio: 0.02–2
alkaline earth metal/Al atomic ratio: 0.03–300, and maintaining the mixture at a temperature and for a period of time sufficient to form crystals of the aluminosilicate. The aluminosilicate is useful as catalyst for converting methanol and/or dimethyl ether into lower olefins.

5 Claims, 1 Drawing Figure

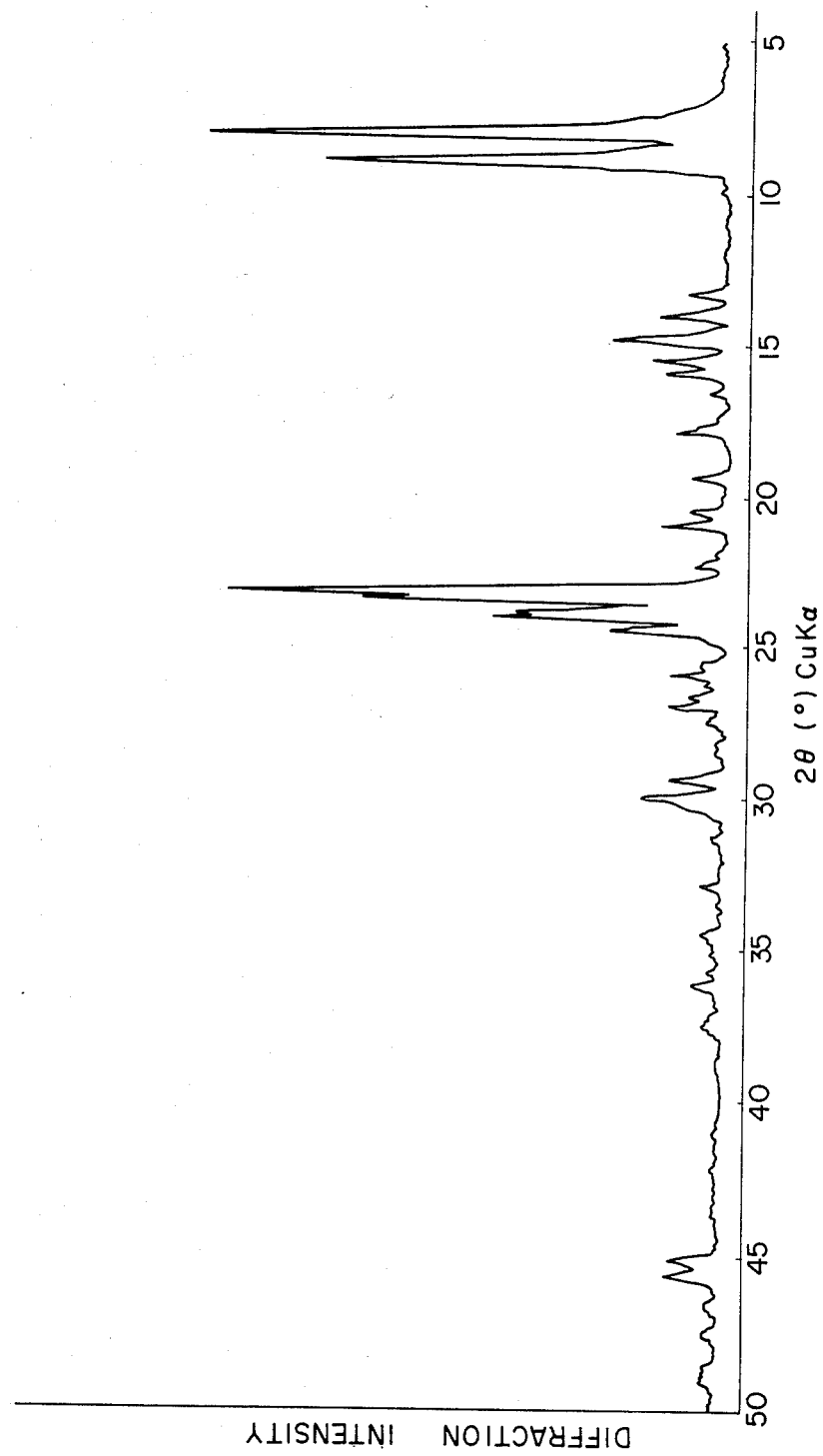

CRYSTALLINE ZEOLITE, METHOD OF PREPARING SAME AND PROCESS FOR THE PRODUCTION OF OLEFINS USING SAME AS CATALYST

BACKGROUND OF THE INVENTION

This invention relates to a novel synthetic aluminosilicate zeolite and a method of preparing such a zeolite material. The present invention is also directed to a process for the production of lower olefins from methanol and/or dimethyl ether with the use of such a zeolite material as catalyst.

It is known in the art that hydrocarbons can be produced by catalytic conversion of methanol and/or dimethyl ether. It is also known that zeolite materials can be used for this purpose as catalyst. Crystalline aluminosilicate zeolite materials, which are known as molecular sieves, are made up of an anionic three-dimensional framework of $SiO_4$ and $AlO_4$ cross-linked by the sharing of oxygen atoms, the anionic charge being balanced by the inclusion in the crystal of an exchangeable cation such as an alkali metal cation. Typical of such synthetic crystalline zeolites are "ZSM-5" and "ZSM-34" produced by Mobil Oil Corp. (See, for example, U.S. Pat. No. 3,702,886). Although "ZSM-5" is effective in producing hydrocarbons of up to 10 carbon atoms (gasoline fraction) by conversion of methanol, it is not suited for the conversion of methanol into lower olefins such as ethylene and propylene. "ZSM-34", on the other hand, exhibits a high selectivity to lower olefins. However, it suffers from a drawback that the catalyst life is very short.

SUMMARY OF THE INVENTION

It is, therefore, the prime object of the present invention to provide a novel synthetic zeolite which is effective as catalyst for the conversion of methanol and/or dimethyl ether into lower olefins, especially ethylene and propylene, with a high selectivity and which exhibits the catalytic activity for a long period of process time.

In accomplishing the above object, the present invention provides a crystalline aluminosilicate having the following empirical formula:

$$xM_2O.yM'O.Al_2O_3.zSiO_2.nH_2O$$

wherein M is an exchangeable cation selected from the group consisting of alkali metals, hydrogen and mixtures thereof, M' is an alkaline earth metal, x is between 0 and 1.5, y is between 0.2 and 40, z is between 12 and 3000 and n is between 0 and 40 and wherein $x+y$ is 1.2 or more, said aluminosilicate having the X-ray diffraction lines of Table 1 of the specification.

The aluminosilicate zeolite of the present invention is clearly distinguished from the known zeolite materials in that the former zeolite has such a very high content of alkaline earth metal that the conventional ion exchange technique would unable to introduce. The alkaline earth metal of the zeolite of the present invention cannot be completely exchanged with other cations by the ion exchange technique. Another distinction is that $x+y$ in the zeolite material of this invention is 1.2 or more.

It is known that alkaline earth metal ion can be incorporated into a proton type aluminosilicate by ion exchange techniques. However, it is very difficult to introduce a large amount of alkaline earth metal cation to aluminosilicate by such a technique. Incorporation of such a cation in the amount of 80% of the theoretical amount of ion-exchangeable cations of the aluminosilicate has been the upper limit in practice.

The present inventors have found that the amount of alkaline earth metal cations incorporated into the aluminosilicate can be increased beyond the theoretical amount by adding an alkaline earth metal salt in the reaction mixture containing a tetrapropylammonium compound, alkali metal oxide, alumina, silica and water and subjecting the resultant mixture to hydrothermal treatment conditions. The addition of an alkaline earth metal salt in such a reaction mixture has been considered to adversely affect the crystal growth and to have to be avoided. However, it has been unexpectedly found that the resulting aluminosilicate is very suited as catalyst for various reactions, especially for the conversion of methanol and/or dimethyl ether into lower olefins.

In another aspect, the present invention provides a method of preparing the above aluminosilicate zeolite material. In a further aspect, the present invention provides a process for subjecting methanol and/or dimethyl ether to pyrolysis in the presence of the above catalyst to obtain lower olefins.

BRIEF DESCRIPTION OF THE DRAWING

Other objects, features and advantages of the present invention will become apparent from the detailed description of the present invention which follows, when considered in light of the accompanying drawing, in which the sole FIGURE is an X-ray diffraction pattern of the aluminosilicate according to the present invention.

DETAILED DESCRIPTION OF THE INVENTION

The crystalline aluminosilicate of this invention is prepared by hydrothermally treating a mixture containing water, a tetrapropylammonium compound and a source of an alkali metal oxide, an oxide of silicon an oxide of aluminum and an oxide of an alkaline earth metal. The mixture has the following composition: a $SiO_2/Al_2O_3$ molar ratio of 12–3000, preferably 50–500; a $OH^-/SiO_2$ molar ratio of 0.02–10, preferably 0.1–0.5; a $H_2O/SiO_2$ molar ratio of 1–1000, preferably 30–80; a tetrapropylammonium ion/$SiO_2$ molar ratio of 0.02–2, preferably 0.05–0.5; and an alkaline earth metal/Al atomic ratio of 0.03–300, preferably 0.5–8.

A water glass, a silica sol, a silica gel and silica are illustrative of suitable sources of an oxide of silicon. Aluminum nitrate, aluminum sulfate, sodium aluminate or alumina may be suitably used as the source of an oxide of alumina. Suitable sources of an oxide of alkaline earth metal include organic and inorganic salts of an alkaline earth metal such as acetates, propyonates, chlorides and nitrates. Illustrative of suitable sources of an alkali metal oxide are sodium oxide of a water glass, sodium aluminate, sodium hydroxide, potassium hydroxide, sodium chloride and potassium chloride. The pH of the mixture is preferably about 11 or below. For this purpose, an acid such as hydrochloric acid, sulfuric acid or nitric acid or an alkali such as an alkali metal hydroxide is added to the mixture, if necessary.

The thus prepared mixture is subjected to a hydrothermal treatment to form crystals of the aluminosilicate. Preferably, the mixture is maintained at a temperature of 80°–200° C., more preferably 150°–180° C., for 1–200 hours, preferably 5–50 hours, under pressure or normal pressure with stirring. The reaction product in the form of crystals is separated by filtration or centrifuge and washed with water for the removal of unassociated ions. Drying and calcination of the washed product, generally performed at a temperature of 520° C., give a crystalline aluminosilicate zeolite material of the present invention which is expressed by the aforementioned empirical formula.

The aluminosilicate has a pore diameter of 5–6 Å and the X-ray diffraction lines shown in Table 1 below. In Table 1, the symbols "s", "m" and "w" mean "strong", "medium" and "weak", respectively. The aluminosilicate prior to the calcination does not shown the two diffraction lines at 3.85 and 3.82 Å, but gives its strongest single diffraction line at 3.84 Å.

The aluminosilicate can adsorb paraffin hydrocarbons with or without modestly branched side chains such as n-hexane and 3-methylpentane but is not able to absorb hydrocarbons with a quarternary carbon atom such as 2,2-dimethylbutane.

TABLE 1

| Interplanar spacing d Å | Relative intensity |
|---|---|
| 11.15 ± 0.25 | s |
| 10.03 ± 0.25 | s |
| 7.43 ± 0.2 | w |
| 6.71 ± 0.2 | w |
| 6.36 ± 0.15 | w |
| 5.99 ± 0.15 | w |
| 5.70 ± 0.15 | w |
| 5.57 ± 0.10 | w |
| 4.98 ± 0.10 | w |
| 4.61 ± 0.10 | w |
| 4.36 ± 0.10 | w |
| 4.26 ± 0.10 | w |
| 3.85 ± 0.08 | s |
| 3.82 ± 0.08 | m |
| 3.74 ± 0.06 | m |
| 3.69 ± 0.06 | w |
| 3.44 ± 0.06 | w |
| 3.35 ± 0.06 | w |
| 3.31 ± 0.06 | w |
| 3.05 ± 0.06 | w |
| 2.99 ± 0.04 | w |
| 2.96 ± 0.04 | w |
| 2.01 ± 0.04 | w |
| 1.99 ± 0.04 | w |

The alkali metal ions and alkaline earth metal ions of the aluminosilicate can be ion-exchanged with proton. While the alkali metal ions may be entirely ion-exchanged with proton, the alkaline earth metal ions are unable to be completely ion-exchanged with proton. In this respect the aluminosilicate of the present invention is distinguished from the conventional alkaline earth metal-carrying aluminosilicate obtained by contacting aluminosilicate of a proton type or alkali metal type with alkaline earth metal ions for ion-exchange therewith. The alkaline earth metal ions of the conventional aluminosilicate are easily and completely ion exchanged with other cations.

The ion exchange with proton may be performed in any known manner. For example, the aluminosilicate is treated with an aqueous solution of an ammonium compound such as ammonium chloride so that the alkali metal ions may be ion exchanged with ammonium ions. The resulting product is then washed, dried and calcined for the elimination of ammonia. Alternately, the ion exchange may be effected by treatment with hydrochloric acid followed by washing, drying and calcination. In either case, the calcination is generally performed at a temperature of 300°–700° C. for 1–100 hours. As described previously, a part of the alkaline earth metal ions is also exchanged with proton through the above treatment. If desired, the proton type aluminosilicate may be further modified with ammonium or metal ions by way of ion exchange or impregnation. Examples of such metals include alkali metals, alkaline earth metals, Fe, Co, Ni, Zn, Mn, Th and rare earth elements such as La.

The aluminosilicate of the present invention may be used as catalyst for decomposition, isomerization, alkylation and polymerization. It is best suited as catalyst for the conversion of methanol and/or dimethyl ether into lower olefins, however. The aluminosilicate of the present invention may be used either by itself or, if desired, in combination with other substances such as clay, kaolin and alumina.

A process for the production of lower olefins from methanol and/or dimethyl ether with the use of the aluminosilicate of the present invention as catalyst includes contacting a gas stream containing methanol and/or dimethylether with the aluminosilicate catalyst at a temperature of 300°–650° C., preferably 350°–600° C., a pressure of 0.1–100 atm, preferably 0.5–10 atm. with a liquid hourly space velocity of 0.1–20 hr$^{-1}$, preferably 1–10 hr$^{-1}$. The gas stream may also contain steam, nitrogen, argon or like inert gas. The reaction can be effected in any suitable system such as a fixed bed, a fluidized bed or a moving bed system.

The catalytic reactions of methanol and/or dimethyl ether resulting in the formation of olefins are exothermic. Therefore, it is generally advantageous to conduct the reaction at a high temperature so that a small reactor can be used, the reaction rate becomes high and the temperature control becomes easy. However, a temperature over 650° C. is disadvantageous because a special, heat-resisting reactor must be used and because the crystal form of aluminosilicates tend to be deteriorated.

The conventional aluminosilicate catalyst of a proton form without alkaline earth metal cations tends to lose its activity at a temperature of about 510° C. Even when such a catalyst is treated to ion exchange the proton with calcium ions, the catalytic activity of the resultant catalyst is lowered when subjected to a temperature of about 540° C. In contrast, the catalyst of the present invention exhibits higher activity at a temperature of about 500° C. as compared with the conventional aluminosilicate catalyst and the activity is not lowered even at a temperature of about 600° C. Thus, with the catalyst according to the present invention, the reaction can be advantageously carried out at a higher temperature than that with the conventional catalyst. The process of the production of olefins according to the present invention has additional merits that the selectivity to lower olefins is high, the formation of paraffinic hydrocarbons and aromatic hydrocarbons such as benzene and toluene is reduced and the deposition of carbonaceous matters on the catalyst is minimized.

The following examples will further illustrate the present invention.

EXAMPLE 1

Preparation of Aluminosilicate Catalysts 0.75 g of aluminum sulfate nonahydrate and 0.91 g of calcium acetate monohydrate were dissolved in 90 g of water, with which were mixed, with vigorous stirring, 100 g of a water glass solution containing 60 g of a water glass (Cataloid SI-30, made by Shokubai Kasei K.K. and containing 30.5% of $SiO_2$ and 0.42% of $Na_2O$) and 40 g of water. Thereafter, the resulting mixture was mixed with 21.14 g of an aqueous sodium hydroxide solution containing 1.14 g of sodium hydroxide and 20 g of water and then with 38.11 g of a solution consisting of 8.11 g of tetrapropylammonium bromide and 30 g of water to obtain a gel with a molar ratio of $SiO_2$ to $Al_2O_3$ of 300.

The gel was then charged in a 300 ml autoclave and subjected to a hydrothermal treatment at a temperature of 160° C. for 18 hours with stirring. The resulting product was then separated, by means of a centrifugal device, into a liquid phase and a solids phase. The solids phase was washed well with water and dried at 120° C. for 5 hours to obtain a crystalline alumino silicate No. 1. Subsequently, 1 g of the aluminosilicate No. 1 was immersed in 15 ml of 0.6N hydrochloric acid and the mixture was stirred at room temperature for 24 hours. After filtration, the solid phase was washed with water, dried at 120° C. and calcined in the air at 520° C. for 5 hours to obtain a proton-type aluminosilicate No. 1H.

The above procedure was repeated in the same manner as described except that the amount of respective components and/or the kind of the alkaline earth metal compounds were varied as shown in Table 2, thereby to obtain twelve types of aluminosilicates Nos. 2-13 and their corresponding proton-type aluminosilicates Nos. 2H-13H. The amounts of the water glass (60 g), tetrapropylammonium bromide (8.11 g) and water (180 g) in respective reaction mixture subjected to the hydrothermal treatment were the same as described above.

The chemical compositions of the aluminosilicates Nos. 4 and 7 and their corresponding proton-type aluminosilicates Nos. 4H and 7H were analyzed by way of atomic absorption with the results as shown in Table 3. The X-ray diffraction pattern of the aluminosilicate No. 4 is shown in the accompanying drawing. The diffraction pattern was obtained by standard X-ray techniques. The radiation was the K-α doublet of copper. The peak heights I were recorded as a function of $2\theta$, where $\theta$ is the Bragg angle. The relative intensities $100I/I_0$ can be calculated from the recorded chart, where $I_0$ is the intensity of the strongest peak ($2\theta = 23.1$).

COMPARATIVE EXAMPLE 1

Aluminosilicates Nos. cptv. 1 through cptv. 3 were prepared in the same manner as described in Example 1 except that no alkaline earth metal compounds were added to the reaction mixture of the hydrothermal treatment. The amounts of aluminum nitrate and sodium hydroxide were as shown in Table 2. The aluminosilicates Nos. cptv. 1-3 were treated in the same manner as described in Example 1 to obtain proton-type aluminosilicates Nos. cptv. 1H-3H. The chemical composition of the aluminosilicates Nos. cptv. 2, 3, 2H and 3H are shown in Table 3.

The aluminosilicate No. cptv. 1H was further subjected to an ion-exchange treatment. Thus, 5 g of the aluminosilicate No. cptv. 1H and 40 ml of 1N $CaCl_2$ aqueous solution were placed in a flask equipped with a reflux condenser and a stirrer and disposed within an oil bath maintained at 80° C. The mixture was allowed to react for 3 hours. After the removal of the liquid phase by decantation, the resulting aluminosilicate was added with 30 ml of the fresh $CaCl_2$ aqueous solution and treated in the same manner as described above. Such procedures were repeated 20 times. The resultant aluminosilicate was the washed well with water until chloride ion was no longer detected. After being dried, the aluminosilicate was calcined at 500° C. for 3 hours to obtain aluminosilicate No. cptv. 1-Ca whose calcium content was found to be 45% of the theoretical amount of ion-exchangeable cations.

TABLE 2

| Aluminosilicate No. | Amount of $Al(NO_3)_3 \cdot 9H_2O$ (g) | Amount of NaOH (g) | Alkaline earth metal compound Chemical formula | Amount (g) |
|---|---|---|---|---|
| 1 | 0.75 | 1.14 | $Ca(CH_3COO)_2 \cdot H_2O$ | 0.91 |
| 2 | " | " | " | 1.82 |
| 3 | " | " | " | 3.64 |
| 4 | 1.14 | 1.26 | " | 1.31 |
| 5 | " | " | " | 2.68 |
| 6 | 2.29 | 1.63 | " | 1.34 |
| 7 | " | " | " | 0.77 |
| 8 | 1.14 | 1.26 | $Mg(CH_3COO)_2 \cdot 4H_2O$ | 1.63 |
| 9 | " | " | $Sr(CH_3COO)_2 \cdot \frac{1}{2}H_2O$ | 1.64 |
| 10 | " | " | $Ba(CH_3COO)_2 \cdot H_2O$ | 1.94 |
| 11 | 2.29 | 1.63 | $Sr(CH_3COO)_2 \cdot \frac{1}{2}H_2O$ | 1.64 |
| 12 | 1.14 | 1.26 | $CaCl_2 \cdot 2H_2O$ | 2.24 |
| 13 | 2.29 | 1.63 | $CaCl_2 \cdot 2H_2O$ | 1.12 |
| cptv. 1 | 0.75 | 1.14 | — | — |
| cptv. 2 | 1.14 | 1.26 | — | — |
| cptv. 3 | 2.29 | 1.63 | — | — |

TABLE 3

| Aluminosilicate No. | $SiO_2$ | $Al_2O_3$ | $Na_2O$ | CaO | Ca/Al |
|---|---|---|---|---|---|
| cptv. 2 | 94.9 | 0.93 | 0.62 | 0 | 0 |
| 4 | 93.6 | 0.86 | 0.21 | 1.30 | 1.4 |
| cptv. 3 | 90.0 | 1.64 | 0.62 | 0 | 0 |
| 7 | 90.2 | 1.57 | 0.32 | 1.43 | 0.8 |
| cptv. 2H | 94.1 | 0.70 | 0 | 0 | 0 |
| 4H | 94.9 | 0.75 | 0 | 0.98 | 1.2 |
| cptv. 3H | 92.6 | 1.36 | 0 | 0 | 0 |
| 7H | 92.8 | 1.42 | 0 | 1.10 | 0.7 |

EXAMPLE 2

Production of Olefins from Methanol

The aluminosilicates Nos. 1H-9H and 11H-12H were used for examining their catalytic performance in converting methanol into olefins. Thus, each aluminosilicate catalyst was shaped into tablets by compression at 400 $Kg/cm^2$ and the resultant tablets were ground into particles. 2 ml of the ground catalyst with a size in the range of 10-20 mesh (Tyler) was packed in a tubular reactor with an inside diameter of 10 mm. Liquid methanol was continuously fed to a vaporizer at a rate of 4 ml/hr and the methanol gas was introduced, at a normal pressure, into the reactor together with argon gas supplied at a rate of 10 ml/min. Thus, the reaction was performed with a liquid hourly space velocity of 2 $Hr^{-1}$. The reaction temperature was stepwise increased from 300° C. up to 600° C. at a rate of 20° C. per 2 hours. The gas discharged from the reactor was occasionally sampled to analyze the composition thereof by gas chromatography. The results are shown in Table 4. Further, the details of the results in the case of using the aluminosilicates Nos. 2H, 4H, 7H, 8H, 9H and 12H are shown in Tables 5-10, respectively. In Tables, the term "Effective Conversion" means a conversion calculated in terms of carbon in which dimethyl ether is regarded as unreacted starting material.

$$\text{Effective Conversion} = 100 - \frac{\text{Amount of Methanol and Dimethyl Ether}}{\text{Amount of Starting Methanol}} \times 100$$

The term "Selectivity" means a selectivity calculated in terms of carbon in which dimethyl ether is regarded as unreacted starting material.

$$\text{Selectivity} = \frac{\text{Yield of the Material Concerned}}{\text{Effective Conversion}} \times 100$$

COMPARATIVE EXAMPLE 2

Example 2 was repeated in the same manner as described using aluminosilicates Nos. cptv. 1H, 2H and 4-Ca. The results were as shown in Table 4 and the detailed results were as shown in Tables 11–13.

TABLE 4

| Catalyst No. | $SiO_2/Al_2O_3$ | M' | $M'O/SiO_2$ | Reaction Temperature (°C.) | Effective Conversion (%) | Selectivity $C_2''$ | $C_3''$ | $(C_2'' + C_3'')$ |
|---|---|---|---|---|---|---|---|---|
| 1H | 300 | Ca | 0.017 | 537 | 100 | 9.5 | 46.8 | 56.3 |
| 2H | 300 | " | 0.033 | 540 | 100 | 11.1 | 43.7 | 54.8 |
| 3H | 300 | " | 0.067 | 540 | 100 | 12.0 | 39.5 | 51.5 |
| 4H | 200 | " | 0.025 | 540 | 100 | 13.9 | 44.7 | 58.6 |
| 5H | 200 | " | 0.050 | 536 | 100 | 12.3 | 47.6 | 59.9 |
| 6H | 100 | " | 0.015 | 540 | 100 | 12.2 | 32.7 | 44.9 |
| 7H | 100 | " | 0.025 | 540 | 100 | 15.5 | 43.8 | 59.3 |
| 8H | 200 | Mg | 0.025 | 497 | 100 | 13.1 | 31.4 | 44.5 |
| 9H | 200 | Sr | 0.025 | 534 | 83.5 | 2.1 | 26.6 | 28.7 |
| 11H | 100 | " | 0.025 | 591 | 100 | 10.0 | 40.8 | 50.8 |
| 12H | 200 | Ca | 0.050 | 554 | 100 | 14.0 | 52.0 | 66.0 |
| 13H | 100 | " | 0.025 | 540 | 100 | 15.0 | 49.4 | 64.4 |
| cptv. 1H | 300 | — | — | 480 | 100 | 11.4 | 29.7 | 41.1 |
|  |  |  |  | 540 | 73.5 | 5.6 | 2.3 | 7.9 |
| cptv. 2H | 200 | — | — | 499 | 100 | 11.6 | 24.2 | 35.8 |
|  |  |  |  | 540 | 100 | 1.2 | 0.7 | 1.9 |
| cptv. 4-Ca | 300 | Ca | ion-exchanged | 500 | 100 | 12.7 | 36.8 | 49.5 |
|  |  |  |  | 540 | 100 | 11.7 | 29.2 | 40.9 |

TABLE 5

Catalyst No. 2H

|  | 360° C. | 400° C. | 440° C. | 500° C. | 540° C. | 560° C. | 600° C. |
|---|---|---|---|---|---|---|---|
| Conversion of methanol | 61.74 | 78.66 | 97.46 | 100.00 | 100.00 | 100.00 | 100.00 |
| Effective Conversion | 0.56 | 12.48 | 95.42 | 100.00 | 100.00 | 100.00 | 100.00 |
| $CO + CO_2$ | 2.32 | 0.64 | 0.12 | 0.30 | 0.45 | 0.77 | 2.03 |
| $CH_4$ | 0 | 0.87 | 0.31 | 0.63 | 0.86 | 1.08 | 2.65 |
| $C_2H_4$ | 1.54 | 5.19 | 3.08 | 6.43 | 11.10 | 13.62 | 17.19 |
| $C_2H_6$ | 0 | 0 | 0.01 | 0.07 | 0.13 | 0.18 | 0.33 |
| $C_3H_6$ | 0 | 22.47 | 30.58 | 41.11 | 43.69 | 44.01 | 40.75 |
| $C_3H_8$ | 0 | 0 | 0 | 0 | 0 | 0 | 0 |
| $C_4H_8$ | 0 | 10.52 | 15.82 | 20.03 | 14.84 | 13.80 | 10.54 |
| $i$-$C_4$ + $nC_4$ | 0 | 1.19 | 3.07 | 1.91 | 1.17 | 0.93 | 0.11 |
| $C_5H_{10}$ | 27.99 | 3.12 | 5.60 | 0.0 | 1.43 | 0.89 | 0.21 |
| $C_5H_{12}$ | 0 | 4.03 | 6.60 | 6.07 | 5.11 | 4.61 | 3.44 |
| B.T.X | 0 | 0 | 1.19 | 1.55 | 9.45 | 7.13 | 11.15 |
| Others | 68.15 | 51.97 | 33.63 | 21.90 | 16.78 | 12.96 | 11.60 |
| $C_2'' + C_3''$ | 1.54 | 27.66 | 33.66 | 47.54 | 54.79 | 57.63 | 57.94 |

TABLE 6

Catalyst No. 4H

|  | 360° C. | 400° C. | 440° C. | 500° C. | 540° C. | 560° C. | 600° C. |
|---|---|---|---|---|---|---|---|
| Conversion of methanol | 19.33 | 62.08 | 77.84 | 100.00 | 100.00 | 100.00 | 100.00 |
| Effective Conversion | 0.03 | 1.24 | 13.57 | 100.00 | 100.00 | 100.00 | 100.00 |
| $CO + CO_2$ | 88.88 | 14.19 | 4.29 | 0.58 | 0.60 | 0.89 | 2.82 |

TABLE 6-continued

Catalyst No. 4H

|  | 360° C. | 400° C. | 440° C. | 500° C. | 540° C. | 560° C. | 600° C. |
|---|---|---|---|---|---|---|---|
| $CH_4$ | 0 | 4.15 | 3.0 | 0.93 | 1.07 | 1.56 | 4.30 |
| $C_2H_4$ | 11.11 | 1.02 | 1.49 | 8.02 | 13.87 | 16.19 | 18.53 |
| $C_2H_6$ | 0 | 0 | 0 | 0.10 | 0.19 | 0.26 | 0.44 |
| $C_3H_6$ | 0 | 0 | 20.62 | 42.98 | 44.69 | 42.62 | 33.22 |
| $C_3H_8$ | 0 | 0 | 0 | 0 | 0 | 0 | 0 |
| $C_4H_8$ | 0 | 0 | 10.74 | 20.41 | 14.37 | 12.42 | 8.86 |
| $i$-$C_4$ + $nC_4$ | 0 | 0 | 1.16 | 1.69 | 1.49 | 0.63 | 0.10 |
| $C_5H_{10}$ | 0 | 0 | 2.35 | 4.59 | 0.91 | 0.63 | 0.57 |
| $C_5H_{12}$ | 0 | 12.37 | 4.85 | 5.95 | 4.98 | 4.18 | 2.86 |
| B.T.X | 0 | 5.09 | 0 | 2.38 | 5.75 | 19.37 | 12.99 |
| Others | 0 | 62.88 | 51.50 | 12.36 | 12.17 | 1.25 | 15.32 |
| $C_2'' + C_3''$ | 11.11 | 1.02 | 22.11 | 51.00 | 58.56 | 58.81 | 51.75 |

TABLE 7

Catalyst No. 7H

|  | 360° C. | 400° C. | 440° C. | 500° C. | 540° C. |
|---|---|---|---|---|---|
| Conversion of Methanol | 10.59 | 48.32 | 78.25 | 100.00 | 100.00 |
| Effective Conversion | 0.66 | 1.68 | 5.10 | 100.00 | 100.00 |
| $CO + CO_2$ | 3.13 | 5.81 | 9.02 | 0.57 | 0.64 |
| $CH_4$ | 0 | 2.36 | 6.64 | 0.61 | 0.81 |
| $C_2H_4$ | 0 | 0.51 | 0.82 | 9.60 | 15.45 |
| $C_2H_6$ | 0 | 0 | 0 | 0.10 | 0.19 |
| $C_3H_6$ | 0 | 0 | 9.96 | 41.78 | 43.76 |
| $C_3H_8$ | 0 | 0 | 0 | 0.01 | 0.03 |
| $C_4H_8$ | 0 | 0 | 5.40 | 20.87 | 13.89 |
| $i$-$C_4$ + $nC_4$ | 0 | 0 | 0 | 2.20 | 1.61 |
| $C_5H_{10}$ | 38.90 | 1.85 | 1.43 | 2.89 | 1.50 |
| $C_5H_{12}$ | 0 | 4.98 | 1.24 | 6.23 | 4.97 |
| B.T.X | 57.97 | 0.89 | 0 | 3.07 | 5.97 |
| others | 0 | 83.58 | 65.50 | 12.17 | 11.17 |
| $C_2'' + C_3''$ | 0 | 0.51 | 10.78 | 51.38 | 59.21 |

TABLE 8

Catalyst No. 8H

|  | 360° C. | 400° C. | 440° C. | 497° C. | 537° C. | 560° C. | 598° C. |
|---|---|---|---|---|---|---|---|
| Conversion of methanol | 99.29 | 100 | 100 | 100 | 100 | 100 | 91.3 |
| Effective Conversion | 99.3 | 100 | 100 | 100 | 100 | 99.9 | 77.4 |
| $CO + CO_2$ | 0 | 0 | 0.1 | 1.0 | 2.9 | 5.3 | 18.8 |
| $CH_4$ | 0.3 | 0.3 | 0.8 | 2.7 | 5.4 | 9.2 | 20.7 |
| $C_2H_4$ | 8.1 | 6.1 | 8.6 | 13.1 | 14.7 | 12.4 | 8.4 |
| $C_2H_6$ | 0.1 | 0.1 | 0.2 | 0.3 | 0.4 | 0.5 | 0.8 |
| $C_3H_6$ | 9.7 | 17.1 | 25.4 | 31.4 | 33.9 | 27.6 | 14.4 |

TABLE 8-continued

| | \multicolumn{7}{c}{Catalyst No. 8H} |
|---|---|---|---|---|---|---|---|
| | 360° C. | 400° C. | 440° C. | 497° C. | 537° C. | 560° C. | 598° C. |
| $C_3H_8$ | 2.1 | 2.5 | 2.4 | 1.4 | 0.4 | 0 | 0 |
| $C_4H_8$ | 12.6 | 16.8 | 19.0 | 16.9 | 13.0 | 9.7 | 5.4 |
| i-$C_4$ + n$C_4$ | 11.5 | 11.0 | 7.6 | 3.2 | 1.5 | 0.9 | 0.3 |
| $C_5H_{10}$ | 4.3 | 2.2 | 0 | 1.3 | 0.8 | 0.5 | 0.5 |
| $C_5H_{12}$ | 10.9 | 9.7 | 7.9 | 5.0 | 3.6 | 2.7 | 1.5 |
| B.T.X | 7.6 | 8.5 | 8.2 | 10.9 | 12.8 | 15.0 | 13.8 |
| Others | 32.8 | 25.7 | 19.8 | 12.8 | | | |
| $C_2''$ + $C_3''$ | 17.8 | 23.2 | 34.0 | 44.5 | 48.6 | 40.0 | 22.8 |

TABLE 9

| | \multicolumn{7}{c}{Catalyst No. 9H} |
|---|---|---|---|---|---|---|---|
| | 360° C. | 401° C. | 441° C. | 501° C. | 534° C. | 559° C. | 599° C. |
| Conversion of methanol | 5.7 | 15.1 | 40.0 | 80.7 | 95.7 | 100 | 100 |
| Effective Conversion | 0.8 | 2.0 | 4.3 | 20.6 | 83.5 | 100 | 100 |
| CO + $CO_2$ | 0 | 0 | 28.2 | 36.8 | 14.6 | 11.6 | 13.6 |
| $CH_4$ | 15.8 | 2.8 | 5.4 | 5.6 | 2.4 | 1.7 | 2.4 |
| $C_2H_4$ | 0 | 0 | 0 | 0 | 2.1 | 4.0 | 7.7 |
| $C_2H_6$ | 0 | 0 | 0 | 0 | 0 | 0.1 | 0.2 |
| $C_3H_6$ | 0 | 1.2 | 7.6 | 8.4 | 26.6 | 33.0 | 33.7 |
| $C_3H_8$ | 0 | 0 | 0 | 0 | 0.2 | 0.2 | 0.2 |
| $C_4H_8$ | 0 | 0 | 2.7 | 5.9 | 16.1 | 16.6 | 15.7 |
| i-$C_4$ + n$C_4$ | 0 | 0 | 0.4 | 0.3 | 0.7 | 0.5 | 0.4 |
| $C_5H_{10}$ | 0 | 0 | 0.7 | 3.5 | 11.0 | 10.3 | 5.5 |
| $C_5H_{12}$ | 0 | 0 | 0 | 0 | 0 | 0 | 0 |
| B.T.X | 0 | 0 | 0 | 0 | 0.3 | 0.6 | 2.6 |
| Others | 84.2 | 96.0 | 55.0 | 39.5 | 26.0 | 21.4 | 18.0 |
| $C_2''$ + $C_3''$ | 0 | 1.2 | 7.6 | 8.4 | 28.7 | 37.0 | 41.4 |

TABLE 10

| | \multicolumn{7}{c}{Catalyst No. 12H} |
|---|---|---|---|---|---|---|---|
| | 360° C. | 400° C. | 440° C. | 500° C. | 540° C. | 560° C. | 600° C. |
| Conversion of Methanol | 60.22 | 82.91 | 95.63 | 100.00 | 100.00 | 100.00 | 100.00 |
| Effective Conversion | 0.04 | 42.61 | 94.08 | 100.00 | 100.00 | 100.00 | 100.00 |
| CO + $CO_2$ | 88.63 | 0.14 | 0.06 | 0.22 | 0.33 | 0.38 | 1.58 |
| $CH_4$ | 0 | 0.28 | 0.27 | 0.55 | 0.76 | 0.98 | 3.58 |
| $C_2H_4$ | 11.36 | 4.88 | 3.29 | 6.50 | 11.33 | 14.01 | 17.78 |
| $C_2H_6$ | 0 | 0 | 0.01 | 0.06 | 0.13 | 0.18 | 0.36 |
| $C_3H_6$ | 0 | 28.48 | 34.85 | 46.53 | 50.64 | 52.04 | 47.01 |
| $C_3H_8$ | 0 | 0 | 0 | 0 | 0 | 0 | 0 |
| $C_4H_8$ | 0 | 12.39 | 15.46 | 19.23 | 18.22 | 17.21 | 12.91 |
| i-$C_4$ + n$C_4$ | 0 | 3.33 | 4.16 | 2.30 | 1.30 | 1.03 | 0.12 |
| $C_5H_{10}$ | 0 | 5.92 | 0 | 0 | 1.69 | 1.17 | 0.70 |
| $C_5H_{12}$ | 0 | 6.83 | 8.19 | 7.01 | 5.99 | 5.52 | 4.15 |
| B.T.X | 0 | 2.04 | 1.48 | 1.81 | 3.94 | 4.05 | 6.06 |
| others | 0 | 35.69 | 32.22 | 15.77 | 5.67 | 3.44 | 5.73 |
| $C_2''$ + $C_3''$ | 11.36 | 33.36 | 38.14 | 53.03 | 61.97 | 66.05 | 64.79 |

TABLE 11

| | \multicolumn{6}{c}{Catalyst No. cptv. 1H} |
|---|---|---|---|---|---|---|
| | 360° C. | 390° C. | 450° C. | 480° C. | 509° C. | 540° C. |
| Conversion of methanol | 100.00 | 100.00 | 100.00 | 100.00 | 72.89 | 73.51 |
| Effective Conversion | 100.00 | 100.00 | 100.00 | 100.00 | 18.92 | 15.36 |
| CO + $CO_2$ | 0 | 0 | 0 | 0.22 | 24.12 | 21.16 |
| $CH_4$ | 0.30 | 0.43 | 1.94 | 4.00 | 42.13 | 44.22 |
| $C_2H_4$ | 7.73 | 6.36 | 9.51 | 11.35 | 7.64 | 5.55 |
| $C_2H_6$ | 0.12 | 0.14 | 0.29 | 0.37 | 1.47 | 1.24 |
| $C_3H_6$ | 9.88 | 14.66 | 25.80 | 29.66 | 4.05 | 2.33 |
| $C_3H_8$ | 2.09 | 2.09 | 1.29 | 0.71 | 0.00 | 0.00 |
| $C_4H_8$ | 12.73 | 15.15 | 17.70 | 16.42 | 1.99 | 0.56 |
| i-$C_4$ + n$C_4$ | 10.15 | 9.65 | 4.86 | 2.70 | 0 | 0 |
| $C_5H_{10}$ | 4.69 | 3.45 | 2.13 | 1.62 | 0.96 | 0 |
| $C_5H_{12}$ | 9.70 | 9.50 | 6.72 | 5.25 | 1.24 | 0.35 |

TABLE 11-continued

| | \multicolumn{6}{c}{Catalyst No. cptv. 1H} |
|---|---|---|---|---|---|---|
| | 360° C. | 390° C. | 450° C. | 480° C. | 509° C. | 540° C. |
| B.T.X | 8.68 | 8.87 | 8.47 | 8.75 | 16.40 | 3.27 |
| Others | 33.94 | 29.70 | 21.29 | 18.96 | 0 | 21.32 |
| $C_2''$ + $C_3''$ | 17.61 | 21.02 | 35.31 | 41.01 | 11.69 | 7.88 |

TABLE 12

| | \multicolumn{5}{c}{Catalyst No. cptv. 2H} |
|---|---|---|---|---|---|
| | 360° C. | 400° C. | 440° C. | 500° C. | 540° C. |
| Conversion of methanol | 100.00 | 100.00 | 100.00 | 100.00 | 100.00 |
| Effective Conversion | 100.00 | 100.00 | 100.00 | 100.00 | 100.00 |
| CO + $CO_2$ | 0.02 | 0.19 | 1.33 | 21.60 | 75.35 |
| $CH_4$ | 0.25 | 0.45 | 1.73 | 13.10 | 22.03 |
| $C_2H_4$ | 6.46 | 6.39 | 9.26 | 11.55 | 1.21 |
| $C_2H_6$ | 0.13 | 0.17 | 0.29 | 0.43 | 0.04 |
| $C_3H_6$ | 9.73 | 15.98 | 23.53 | 24.22 | 0.67 |
| $C_3H_8$ | 2.80 | 3.13 | 3.02 | 0.22 | 0.00 |
| $C_4H_8$ | 11.71 | 14.62 | 16.10 | 9.59 | 0.06 |
| i-$C_4$ + n$C_4$ | 12.45 | 11.85 | 8.36 | 2.02 | 0 |
| $C_5H_{10}$ | 4.09 | 1.76 | 0 | 0.71 | 0.15 |
| $C_5H_{12}$ | 10.27 | 9.86 | 7.81 | 3.12 | 0 |
| B.T.X | 10.53 | 11.47 | 10.69 | 7.56 | 0.50 |
| Others | 31.57 | 24.12 | 17.88 | 5.89 | 0.0 |
| $C_2''$ + $C_3''$ | 16.19 | 22.37 | 32.79 | 35.77 | 1.88 |

TABLE 13

| | \multicolumn{5}{c}{Catalyst No. cptv. 4-Ca} |
|---|---|---|---|---|---|
| | 360° C. | 400° C. | 440° C. | 500° C. | 540° C. |
| Conversion of methanol | 100.00 | 100.00 | 100.00 | 100.00 | 100.00 |
| Effective Conversion | 100.00 | 100.00 | 100.00 | 100.00 | 100.00 |
| CO + $CO_2$ | 0 | 0 | 0 | 0.06 | 1.51 |
| $CH_4$ | 0.27 | 0.38 | 0.79 | 3.21 | 9.83 |
| $C_2H_4$ | 9.80 | 6.72 | 8.13 | 12.69 | 11.70 |
| $C_2H_6$ | 0.12 | 0.11 | 0.17 | 0.38 | 0.58 |
| $C_3H_6$ | 11.19 | 18.30 | 27.63 | 36.75 | 29.20 |
| $C_3H_8$ | 1.58 | 1.47 | 1.61 | 0.69 | 0.0 |
| $C_4H_8$ | 13.21 | 17.01 | 19.84 | 17.58 | 8.77 |
| i-$C_4$ + n$C_4$ | 10.04 | 9.31 | 6.41 | 2.68 | 1.07 |
| $C_5H_{10}$ | 5.23 | 0 | 4.99 | 1.84 | 2.43 |
| $C_5H_{12}$ | 10.29 | 9.63 | 8.05 | 5.14 | 3.29 |
| B.T.X | 7.54 | 7.31 | 5.60 | 13.92 | 13.76 |
| Others | 30.74 | 29.76 | 16.78 | 5.07 | 17.86 |
| $C_2''$ + $C_3''$ | 20.99 | 25.02 | 35.76 | 49.44 | 40.90 |

We claim:

1. A process for subjecting methanol and/or dimethyl ether to pyrolysis to obtain olefins, comprising contacting a gas stream containing methanol and/or dimethyl ether with a catalyst which is crystalline aluminosilicate having the following empirical formula:

$$xM_2O \cdot yM'O \cdot Al_2O_3 \cdot zSiO_2 \cdot nH_2O$$

wherein M is an exchangeable cation selected from the group consisting of alkali metals, hydrogen and mixtures thereof, M' is Ca or Sr, x is a number of between 0 and 1.5, y is a number of between 1.4 and 40, z is a number of between 97.7 and 3000 and n is a number of between 0 and 40 and wherein x+y is at least 1.4, said aluminosilicate having the x-ray diffraction lines of Table 1 of the specification.

2. A process as claimed in claim 1, wherein said contact is carried out at a temperature of 300°-650° C., a pressure of 0.1-100 atm and a liquid space velocity of 0.1-20 $hr^{-1}$.

3. A process as claimed in claim 1, wherein said catalyst is that obtained by a method comprising the steps of providing a reaction mixture containing water, a tetrapropylammonium compound and a source of an alkali metal oxide, an oxide of silicon, an oxide of aluminum and an oxide of Ca or Sr and having a composition falling within the following ranges:

$SiO_2/Al_2O_3$ molar ratio: 97.7–3000
$OH^-/SiO_2$ molar ratio: 0.02–10
$H_2O/SiO_2$ molar ratio: 1–1000
tetrapropylammonium ion/$SiO_2$ molar ratio: 0.02–2
alkaline earth metal/Al atomic ratio: 0.03–300, and maintaining said mixture at a temperature and for a period of time sufficient to form crystals of said aluminosilicate.

4. A process as claimed in claim 1 wherein M is hydrogen and is at least partially replaced by a metal selected from the group consisting of alkali metals, alkaline earth metals, Fe, Co, Ni, Zn, Mn, Th and the rare earth elements.

5. A process as claimed in claim 1 wherein M' is Ca.